(12) United States Patent
Ward et al.

(10) Patent No.: US 7,225,008 B1
(45) Date of Patent: May 29, 2007

(54) MULTIPLE USE ANALYTE SENSING ASSEMBLY

(75) Inventors: W. Kenneth Ward, Portland, OR (US); Richard G. Sass, Portland, OR (US)

(73) Assignee: iSense Corporation, Portland, OR (US)

( * ) Notice: Subject to any disclaimer, the term of this patent is extended or adjusted under 35 U.S.C. 154(b) by 680 days.

(21) Appl. No.: 10/464,820

(22) Filed: Jun. 17, 2003

Related U.S. Application Data (60) Provisional application No. 60/473,013, filed on May 21, 2003, provisional application No. 60/473,014, filed on May 21, 2003.

(51) Int. Cl.
*A61B 5/05* (2006.01)

(52) U.S. Cl. ............... 600/345; 600/347; 600/365; 204/403.01; 204/403.03; 29/868; 29/33 F (58) Field of Classification Search ............ 204/403.03
See application file for complete search history.

(56) References Cited

U.S. PATENT DOCUMENTS

| | | | | |
|---|---|---|---|---|
| 4,953,552 A | 9/1990 | DeMarzo | ............... | 128/635 |
| 5,165,407 A | 11/1992 | Wilson et al. | ............... | 128/635 |
| 5,395,504 A * | 3/1995 | Saurer et al. | ............ | 204/403.03 |
| 5,428,123 A | 6/1995 | Ward et al. | ............... | 528/28 |
| 5,510,266 A | 4/1996 | Bonner et al. | ............... | 436/43 |
| 5,660,163 A | 8/1997 | Schulman et al. | ............ | 126/635 |
| 5,871,494 A | 2/1999 | Simons et al. | ............ | 606/181 |
| 6,051,392 A | 4/2000 | Ikeda et al. | ............ | 435/25 |
| 6,228,100 B1 | 5/2001 | Schraga | | |
| 6,309,351 B1 | 10/2001 | Kurnik et al. | ............ | 600/309 |
| 6,352,514 B1 | 3/2002 | Douglas et al. | ............ | 600/583 |
| 6,477,395 B2 | 11/2002 | Schulman et al. | ............ | 600/345 |
| 6,484,046 B1 | 11/2002 | Say et al. | ............ | 600/345 |
| 6,534,017 B1 | 3/2003 | Bottwein et al. | ............ | 422/104 |
| 6,540,890 B1 * | 4/2003 | Bhullar et al. | ......... | 204/403.02 |
| 6,592,745 B1 | 7/2003 | Feldman et al. | ......... | 205/777.5 |
| 6,988,996 B2 | 1/2006 | Roe | | |
| 2003/0211619 A1 * | 11/2003 | Olson et al. | ............ | 436/44 |
| 2004/0253624 A1 * | 12/2004 | Smith et al. | ............ | 435/6 |

FOREIGN PATENT DOCUMENTS

| | | |
|---|---|---|
| WO | WO 01/73124 A2 | 4/2001 |
| WO | WO 01/64105 A1 | 7/2001 |

\* cited by examiner

*Primary Examiner*—Patricia Mallari
(74) *Attorney, Agent, or Firm*—Schwabe Williamson & Wyatt (57) ABSTRACT

A method of making a multiple use analyte sensing assembly. The method includes placing a coated wire analyte sensing assembly on an article having a surface that defines a set of pockets so that the wire extends into each pocket. The coated wire is then typically covered by a layer of insulation material between pockets, either by placing an apertured insulation material layer over the pockets so that the apertures correspond to the pockets or by placing a liquid curable insulation material over the coated wire between pockets.

17 Claims, 9 Drawing Sheets

MULTIPLE USE ANALYTE SENSING ASSEMBLY

RELATED APPLICATIONS

This application claims priority from provisional applications Ser. No. 60/473,013 and 60/473,014, both of which were filed on May 21, 2003 and both of which are incorporated by reference as if fully set forth herein.

BACKGROUND OF THE INVENTION

Currently available multiple use glucose sensing assemblies rely on a multiplicity of individual sensing elements, currently in the form of strips of coated paper, each one bearing electrical contacts. As multiple use glucose sensing assemblies become more common, the issue of the expense of the individual sensing elements used in these assemblies becomes an increasingly important issue. Currently available sensing assemblies that contain an array of single use sensors typically cost on the order of $0.80 per measurement. Over the years this expense can increment to a considerable sum. A serious health concern arises from this expense because a diabetic patient might refrain from taking a blood glucose measurement that he would otherwise take, due to the expense of taking the measurement. In some instances the failure to take a blood glucose measurement could be fatal. Moreover, the more measurements a diabetic patient takes, the better understanding she will gain of the relationship between her insulin injection schedule; her food intake, stress and exercise levels; and her blood glucose level.

A number of impediments, however, stand in the way of arriving at a truly economical multi-use sensing assembly. Assemblies that use chemical coated paper strips must be refilled with these strips.

Another type of assembly (a "coated wire assembly") uses a wire having an electrochemically active metal (typically platinum) that is largely coated with insulation. A portion of this insulation is removed to form an electrode that is then covered with a assembly of membranes that produces an electric current when the analyte of interest (typically glucose) is present. In the production of a coated wire assembly it has been found that a problem is created in the removal of the wire insulation. With respect to insulated wires it has been found that the insulation is generally not applied in a truly concentric manner. Accordingly, if a laser beam is used to remove the insulation it tends to pit and stipple the electrochemically active surface of the wire, increasing its surface area. Although a large surface area is typically desirable, the process is unpredictable because of the unevenness of the insulation coat. As a result a non-uniformity is introduced into each set of sensing elements.

Another problem found in a coated wire system is encountered when a separate coated wire segment is used for each measurement. In this case, each coated wire segment must be carefully individually created by dip coating. Moreover, each individual coated wire segment must be brought into contact with body fluid, implying some means of retaining and moving the coated wire segments.

For a multiple use sensing assembly, because there is no calibration procedure, differing sensitivities at the various sensing sites result in a lack of repeatability in the formation of measurement and resultant inaccuracies.

Accordingly, a method of making a multiple use analyte sensing assembly that does not rely on chemical strips and that does not require the stripping away of an insulation layer from an underlying conductor is desirable.

SUMMARY

In a first separate aspect, the present invention is a method of making a multiple use analyte sensing assembly. The method includes placing a coated wire analyte sensing assembly in an article having a surface defining a set of blood pockets so that a portion of the wire is present in each pocket.

In a second separate aspect the present invention is a multiple use analyte sensing assembly, comprising an article having a surface defining a set of pockets, and including a pocket assembly for each pocket. Each pocket assembly includes an analyte sensing active electrode, a reference electrode and a lancet. The sensing assembly also includes a housing having a housing aperture and an article movement assembly adapted to move the article relative to the housing so that each pocket assembly may be moved, in sequence, into alignment to the housing aperture.

In a third separate aspect the present invention is a method of forming multiple measurements of concentration of an analyte in animal (typically human) tissue. The method uses a multiple-use analyte concentration measurement assembly that has a lengthwise conductive element that traverses a plurality of blood pockets and also has an effective reference electrode. A first blood pocket current measurement is formed by filling a first blood pocket with blood and placing a voltage on the lengthwise conductive element, relative to an effective reference electrode, to form a first blood pocket current measurement at the first blood pocket. Just before using the second blood pocket, a voltage is again placed on the lengthwise conductive element, relative to an effective reference electrode, and a baseline current measurement is formed. Immediately after forming the baseline current measurement a second blood pocket is filled with blood and a voltage is placed on the lengthwise conductive element, relative to an effective reference electrode, to form a second blood pocket current measurement. Finally, the baseline current measurement is subtracted from the second blood pocket current measurement to form a corrected second blood pocket current measurement.

In a fourth separate aspect, the present invention is a method of forming multiple measurements of concentration of an analyte in animal (typically human) tissue. A multiple use analyte concentration measurement assembly having a plurality of lengthwise conductive elements each of which traverses a plurality of blood pockets is used. Each blood pocket has an effective reference electrode. A first current measurement is taken in a blood pocket traversed by a first conductive element. Then, a second, immediately subsequent, current measurement is taken in a blood pocket traversed by a second conductive element.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENTS

Figures 1, 2:
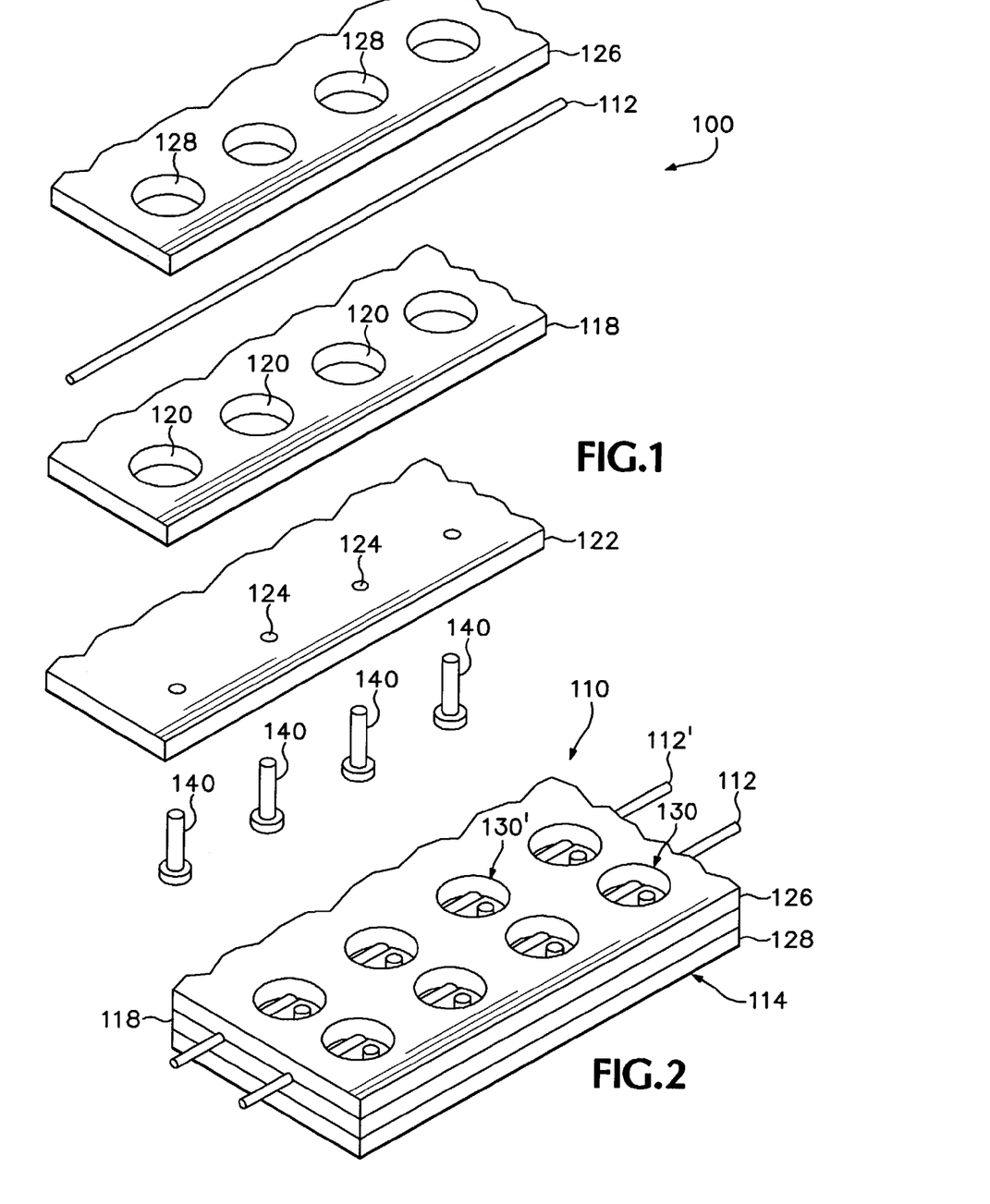
FIG. 1 is an exploded perspective view of an alternative embodiment of a multiple use analyte sensing assembly according to the present invention.
FIG. 2 is a perspective view of the analyte sensor of FIG. 1.
Figure 3:
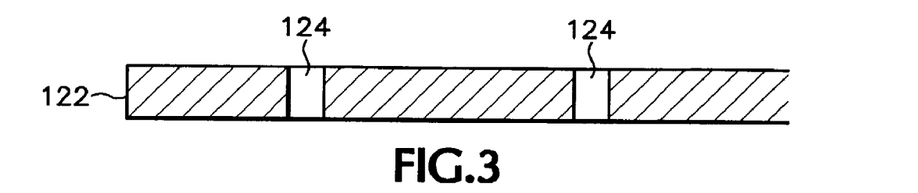
FIG. 3 is a side sectional view of a work piece that represents a step in the manufacture of the multiple use analyte sensing assembly of FIG. 1.
Figure 4:
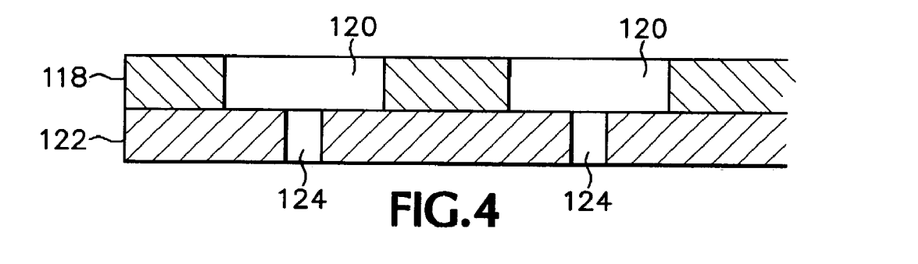
FIG. 4 is a side sectional view of a work piece that represents a further step in the manufacture of the multiple use analyte sensing assembly of FIG. 1.
Figure 5:
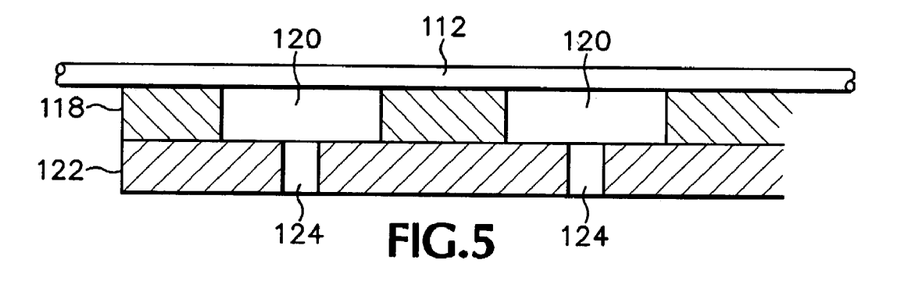
FIG. 5 is a side sectional view of a work piece that represents a still further step in the manufacture of the multiple use analyte sensing assembly of FIG. 1.
Figure 6:
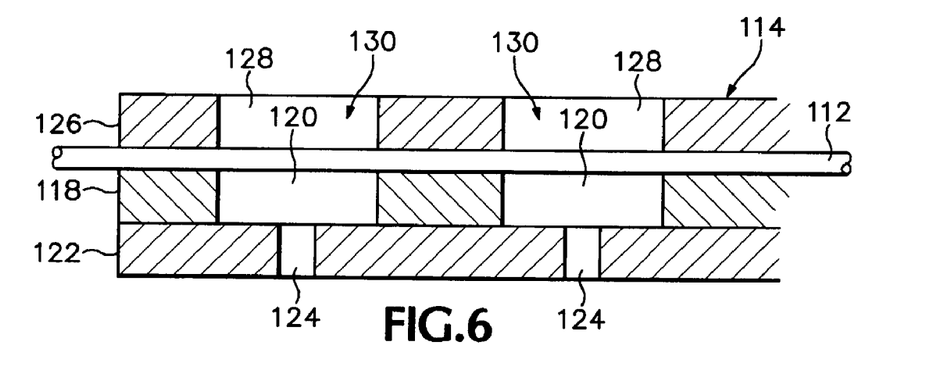
FIG. 6 is a side sectional view of the analyte sensing assembly of FIG. 1.

In broad overview, the embodiment of FIGS. 1-7 is shown in FIG. 2, as a multiple use blood glucose assembly in which a sensing wire assembly 112 traverses a set of pockets 130 that are blood-tight with respect to one another. The pockets 130 are used in sequence, with a segment of the wire assembly 112 that passes through the particular pocket being used as an indicating electrode, with the current flowing out of that portion of the wire being derived by measurements and calculation to provide an estimate of the concentration of glucose in the blood. The construction of this assembly, together with a discussion of how the various technical problems that arise in the use of such an assembly may be resolved, appears below.

Referring to FIGS. 1-7, the production of a multiple use analyte sensing assembly 110 may be started by laminating together a middle sheet 118 having a set of blood receiving apertures 120, placed over a bottom sheet 122 having a set of lancet assembly receiving apertures 124. Then an analyte sensing wire assembly 112 is placed onto middle sheet 118 so that a portion of the wire assembly 112 is included in each of the blood receiving apertures 120.

Figure 13:
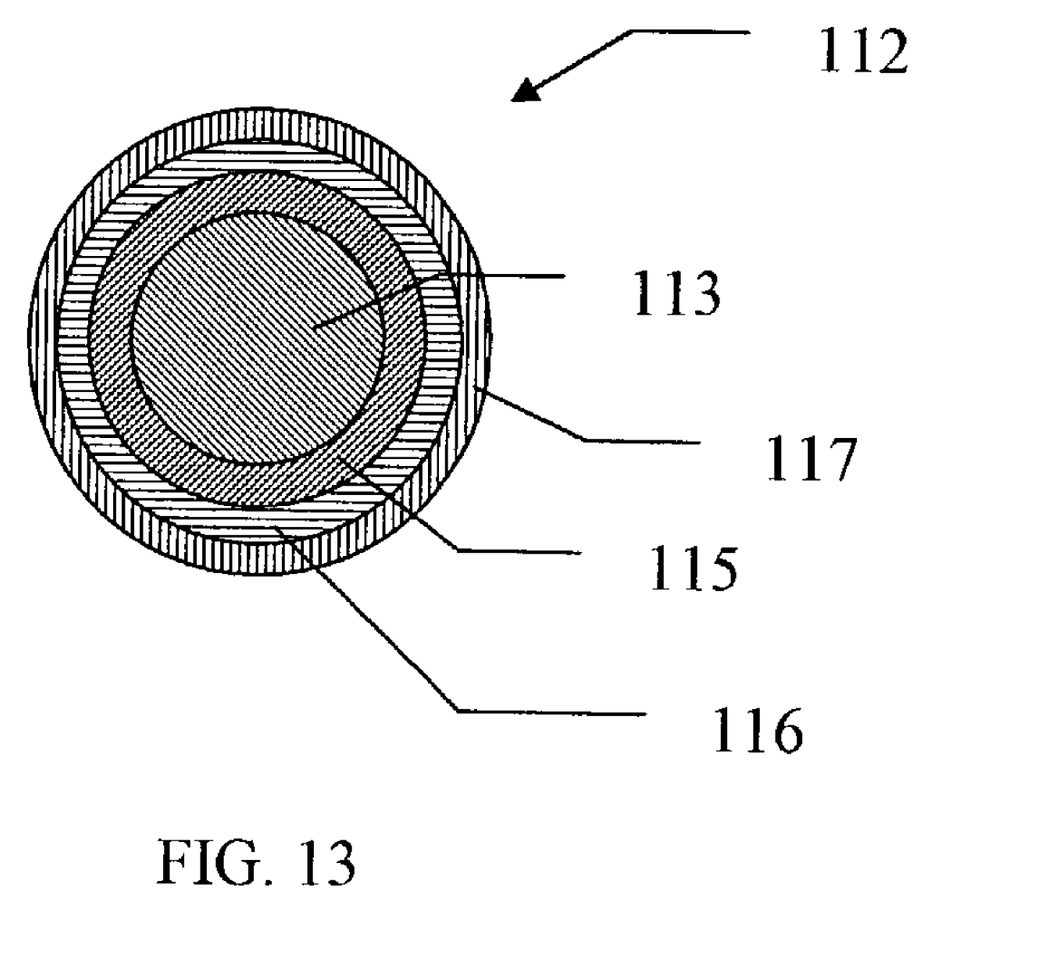
FIG. 13 is a cross-sectional view of a sensing wire assembly, according to the present invention.

Referring to FIG. 13, wire assembly 112 includes a wire 113 coated with a membrane assembly that includes three membranes 115, 116 and 117 adapted to produce an electrical current, when exposed to an analyte bearing fluid, provided that a voltage is present on wire 113, relative to a nearby reference electrode (discussed further below). One such membrane assembly is described in U.S. Pat. No. 5,165,407, issued Nov. 24, 1992. Another such membrane assembly is described in application Ser. No. 10/342,144 filed Jan. 13, 2003, which is assigned to the same assignee as the present application and is incorporated by reference as if fully set forth herein. In one preferred embodiment membrane 115 is an interferent excluding layer made of a material such as sulphonated poly ether sulphone or 3-amino phenol. Membrane 116 is made of an enzyme that reacts with glucose, such as glucose oxidase. Membrane 117 is a permselective layer for ensuring an adequate concentration of oxygen, relative to the concentration of glucose. Membrane 117 may be a copolymer of the type described in U.S. Pat. No. 5,428,123. These membranes may be applied to wire 113 continuously by way of a sequence of baths through which wire 113 is drawn.

Referring again to FIGS. 1-7, the wire assembly 112 is then covered by a top sheet 126 having a set of apertures 128 that are aligned with the apertures 120 of sheet 118 leaving exposed portions of wire assembly 112. When sheets 126, 122, and 118 are assembled together, a set of blood-tight pockets 130, each secured from the others so that blood cannot flow from one pocket 130 to another, are formed from the aligned apertures with portions of wire assembly 112 exposed in each pocket 130. In an alternative embodiment layer 126 is formed from liquid resin or adhesive that is applied onto sheet 118 so that it covers wire assembly 112 between apertures 128, and is then cured.

Figure 8:
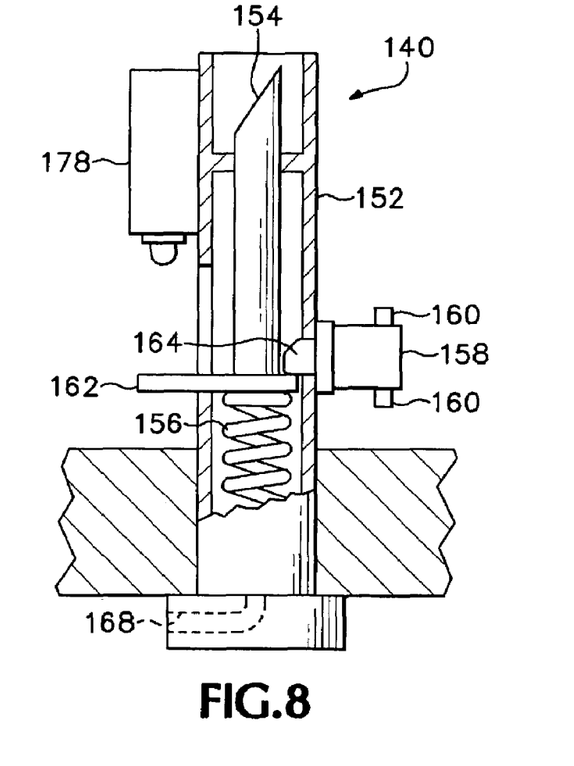
FIG. 8 is a detailed sectional view of a variant of a lancet assembly.

Each small aperture 124 accommodates a spring loaded lancet assembly 140. FIG. 8 shows the lancet assembly 140, in greater detail. Assembly 140 is electrically actuated at a pair of terminals 160. When the voltage across terminals 160 is changed a trip 164 is pulled backwards from a lancet rim 162 by an electric actuator 158, thereby releasing a lancet 154 to travel out of a tube 152, urged forward by a spring 156. In one preferred embodiment actuator 158 is piezoelectric, with the change in voltage across terminals 160 causing a change in size of a piezoelectric element (not shown) resulting in the movement of trip 164. In another embodiment, actuator 158 is a solenoid. In addition, a solenoid assembly 178 pushes back on rim 162 to push lancet 154 back into tube 150, after lancet 154 has been used. Assembly 140 includes an air vent 168, for releasing the air in pocket 130, thereby permitting pocket 130 to fill with blood.

Figure 14:
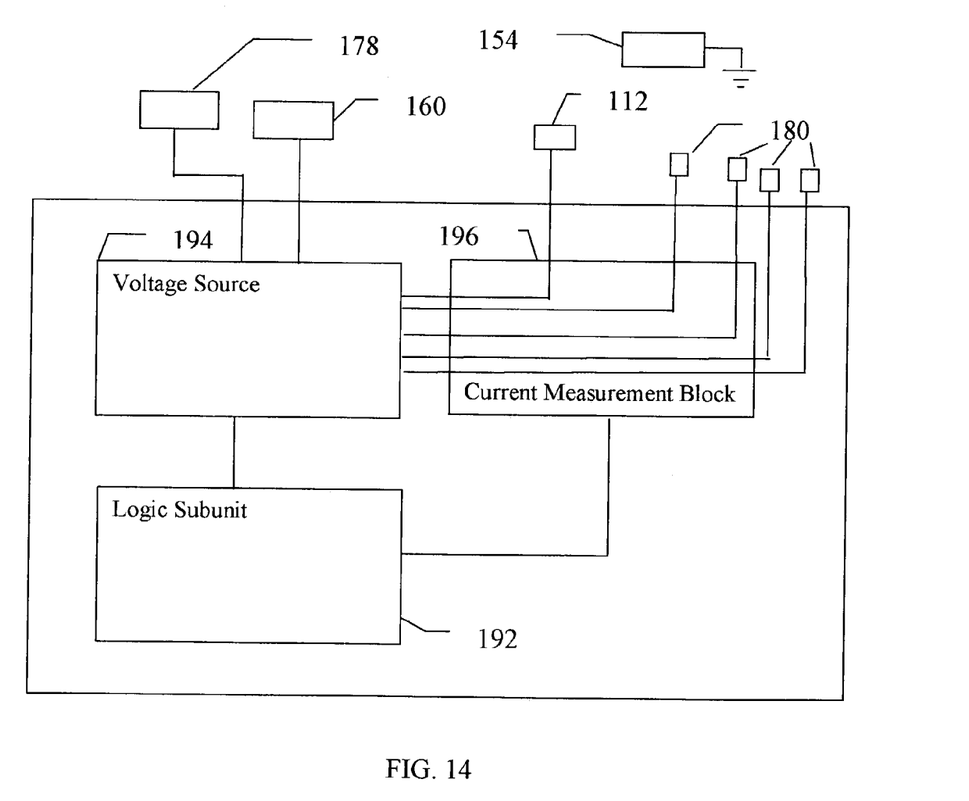
FIG. 14 is a block diagram of the voltage application, current sensing and logic unit of FIG. 7.

A voltage application, current sensing and logic unit 190 controls the operation of assembly 110. Referring to FIG. 14, in greater detail unit 190 is made up of three subunits: a logic subunit 192, a voltage source 194 and a current measurement block 196.

It is most desirable to begin the electrical measurement process as soon as a pocket 130 fills with blood, so that the process may finish as soon as possible but nevertheless preventing the data processing algorithm from receiving early samples, taken before blood has entirely wetted the coated wire assembly 112 traversing the pocket 130. Accordingly, a set of fill sense terminals 180 (FIG. 7) permit associated circuitry that is described further below to detect the moment when pocket 130 is filled with blood, as further described below. Pocket 130 has a volume that is on the order of a microliter to a nanoliter. Accordingly, only about one second is required for pocket 130 to fill with blood.

At any time after the first pocket 130 is used for analyte measurement, a potential problem is caused by signal contamination due to current flowing from wire 113 in any recently used pocket 130, due to remnants of blood that have remained in the recently used pocket 130, which may permit current flow. Accordingly, in one preferred embodiment, unit 190 places a voltage on wire 113, relative to lancet assemblies 140, which serves as a reference electrode, immediately prior to the physical triggering of a particular lancet 154 or later so long as it is done before the blood fills the pocket 130 associated with that lance assembly 140, and any resultant current is measured at that time. This measurement forms a baseline or leakage current representing the current flow through wire 113 due to residual blood in the recently used pockets 130. This measurement is subtracted from the immediately subsequent measurement formed after the release of the lancet 154, to correct for corruption of the current measurement by current in recently used pockets 130 that is not intended to form part of the present-time measurement.

Even though a baseline current measurement can be formed, it is nevertheless desirable to minimize the corrupting effect of recently used blood pockets on each current measurement. Accordingly, in one preferred embodiment there is at least one additional sense conductor or wire assembly 112' and set of pockets 130' that is traversed by wire assembly 112'. Each wire assembly 112' is in a separate circuit, so that immediately after a sample is taken in a first pocket 130, a second sample may be taken in a pocket 130' traversed by separate wire assembly 112', so that the measurement will not be corrupted by the blood drying in pocket 130. The step of taking a baseline or leakage current may still be advisable, as it is possible that a pocket 130', traversed by wire assembly 112', had been recently used. In order to minimize corruption caused by recently used pockets or pockets 130, several different sets of pockets 130' and wires assembly 112' may be included in a single assembly 110.

Figure 7:
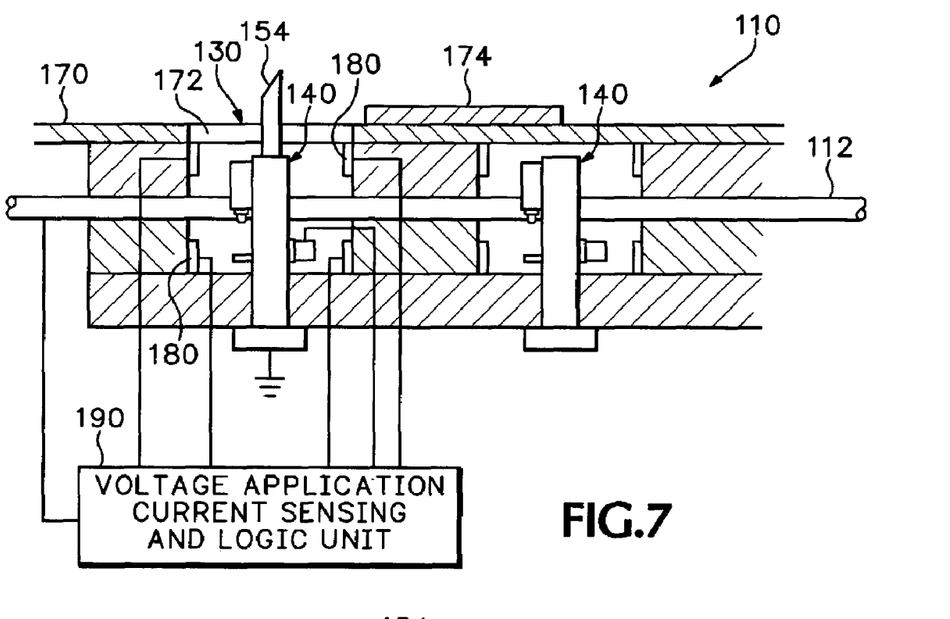
FIG. 7 is a detailed side sectional view of the analyte sensing assembly of FIG. 1, showing one lancet assembly in the lancet protruding state and another lancet assembly in the lancet retracted state.

Referring to FIG. 7 assembly 110 is located in an assembly housing 170, defining an aperture 172. To measure an analyte, such as glucose, assembly 110 is moved within housing 170 so that a fresh lancet assembly 140 is aligned with an aperture 172. In one preferred embodiment, assembly 110 is in the form of a drum. In an additional preferred variant pockets 130 are arranged in a two-dimensional grid with the wire assembly 112 being arranged in a circuitous path to traverse each pocket 130.

Figure 15A:
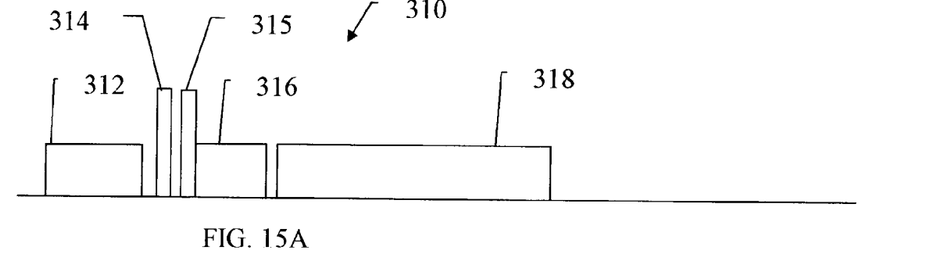
FIG. 15A is a timing diagram of the signals sent from the voltage source of FIG. 14.
Figure 15B:
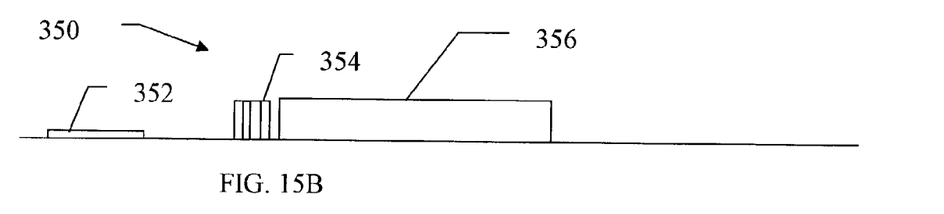
FIG. 15B is a timing diagram of the current measurement of the current measurement block of FIG. 14.

FIGS. 15A and 15B show the timing of the unit 190 outgoing signals 310 and current measurements 350. The measurement process starts when a user presses housing 170 against the skin of a patient and presses a button (not shown). This causes logic unit 192 to command voltage source 194 to place a voltage pulse 312 on wire 113, relative to lancet assembly 140, which is grounded to the housing 170 (typically held in the hand of the patient). Current measurement block 196 detects any resulting current 352 and sends resultant magnitude information to logic unit 192. Next, logic unit 192 commands voltage source 194 to send a pulse 314 to lancet actuator 158, releasing lancet 154, which broaches the skin and causes bleeding. A subsequent pulse 315 sent to an actuator 178 causes lancet 154 to be withdrawn from the skin. A voltage 316 is placed onto the set of blood fill terminals 180, so that as blood fills the pocket 130 and reaches one of the terminals 180 (FIG. 7), a current 354 (shown as a set of overlapping pulses in FIG. 15B) is conducted through the blood to lancet 154, which is grounded (provided that blood has also reached lancet 154).

Current 354 also appears on the wire leading to the terminal 180 and is detected by block 196 and reported to logic subunit 192. When a current appears on each wire leading to a terminal 180 this indicates that pocket 130 is full, regardless of the orientation in which assembly 110 is being held by the user. This condition is detected by logic subunit 192. Subunit 192 then commands voltage source 194 to remove the voltage 316 from terminals 180 and to place 0.6 VDC signal 318 on wire 113, again relative to lancet 154. This creates a current outflow 356 from wire 113 (ultimately received at lancet 154, acting as a reference electrode), which is measured by current measurement block 196. This current measurement is analyzed, together with baseline current measurement 352, to provide an estimate of analyte concentration.

Skilled persons will readily appreciate the advantages of the above described assembly. The coated wire assembly 112 may be created by way of a continuous process, such as drawing the wire successively through a set of baths to build up the system of membranes, or by use of successive extrusion steps. Alternatively, for some membrane assembly variants only one layer of coating may be necessary. Continuous coating techniques are far less expensive than coating techniques used for pieces of wire. Accordingly the cost of each sensing site can be greatly reduced by continuously coating a lengthwise conductor and, as described in this application, covering the entire sensing wire assembly except for in places where body fluid exposure is desired. A voltage is then placed along the entire wire 113, but current only leaves wire 113 where it is touching body fluid. As pockets 130 are on the order of a nano-liter to a micro-liter in volume, they are filled quite rapidly, on the order of a second. Moreover, as such a small amount of blood is used, the blood dries fairly rapidly, thereby avoiding the potential for odor. Also, the wire 113 used is on the order of between 10 and 200 microns thick, thereby minimizing the amount of platinum and other materials, such as sulphonated poly ether sulphone and polyurethane based multi-polymer used. Further, the operations used in the manufacture of assembly 110 are generally susceptible to automation, making possible the rapid production of assemblies 110 at a reasonable price. Finally, because the coating processes are continuous, it is easier to achieve repeatability between a first pit 130 and a second pit 130, than was achievable in previous multiple use assemblies.

In many respects the embodiments discussed above bear the same relationship to existing multiple use glucose measurements systems as a modern cartridge based camera bears to an old style one frame-at-a-time camera. Whereas in the presently available systems the user must cope with a strip of chemically treated paper coming out of the sensor each time a measurement is performed, in the embodiment described above, the user only needs to load drum 114 into the assembly 110 once every month to six months, depending on the design specifics and the need of the user for frequent data. The use of the assembly 110 is fairly effortless, only involving a brief prick from lancet 154.

Referring to FIGS. 9-12, in yet an additional preferred embodiment of a sensing assembly 210, a disk 212 is machined to define a series of pockets 214 arranged circumferentially about a radially exterior portion 216 of disk 212. The control and sensing portions of this embodiment are essentially the same as for the embodiment of FIGS. 1-8 and 13-15B, except as noted below. Exterior portion 216 is made of a resiliently compressible material that in addition to defining pockets 214 also is machined to define a pair of wire slots 218, for receiving and retaining an analyte sensing wire assembly 220, which may be the same as assembly 112, and a simple conductive wire 222, which acts as a reference electrode. Each one of slots 218 is machined to be slightly less wide than the diameter of the wire 220 or 222 that it receives. Accordingly, wires 220 and 222 are affirmatively retained by the pressure of the sides of slots 218. A second set of openings 226 exposes wires 220 and 222 so that they can be contacted by a first contact 240 and a second contact 242, which are moved to make contact with wire segments 220 and 222, respectively, each time disk 216 is moved to place a new pocket 214 into position near a housing aperture 172. In this manner, signal contamination from drying blood in a recently used pocket 214 or pockets 214 is avoided as there is no electrical connection between pockets. Accordingly, there is no need for the data collection and processing for forming and using a baseline current measurement that is described for the embodiment of FIGS. 1-8 and 13-15B. Alternatively, wires 220 and 222 are continuous or are divided into several sections, each of which traverses several pockets 214 and are controlled as is described for assembly 112.

Disk 212 is positioned in a housing 270 having an aperture 272 and travels in a rotational direction 274. A dam 276 on the rim of each pocket 214 prevents blood from the pockets 214 that have been used for blood measurement from contaminating unused pockets 214. In an alternative embodiment, all of the unused pockets 214 are electrically connected together by wires 220 and 222 but after being used wires 220 and 222 are severed between the most recently used pocket 214 and the adjacent unused pocket 214.

Figure 9:
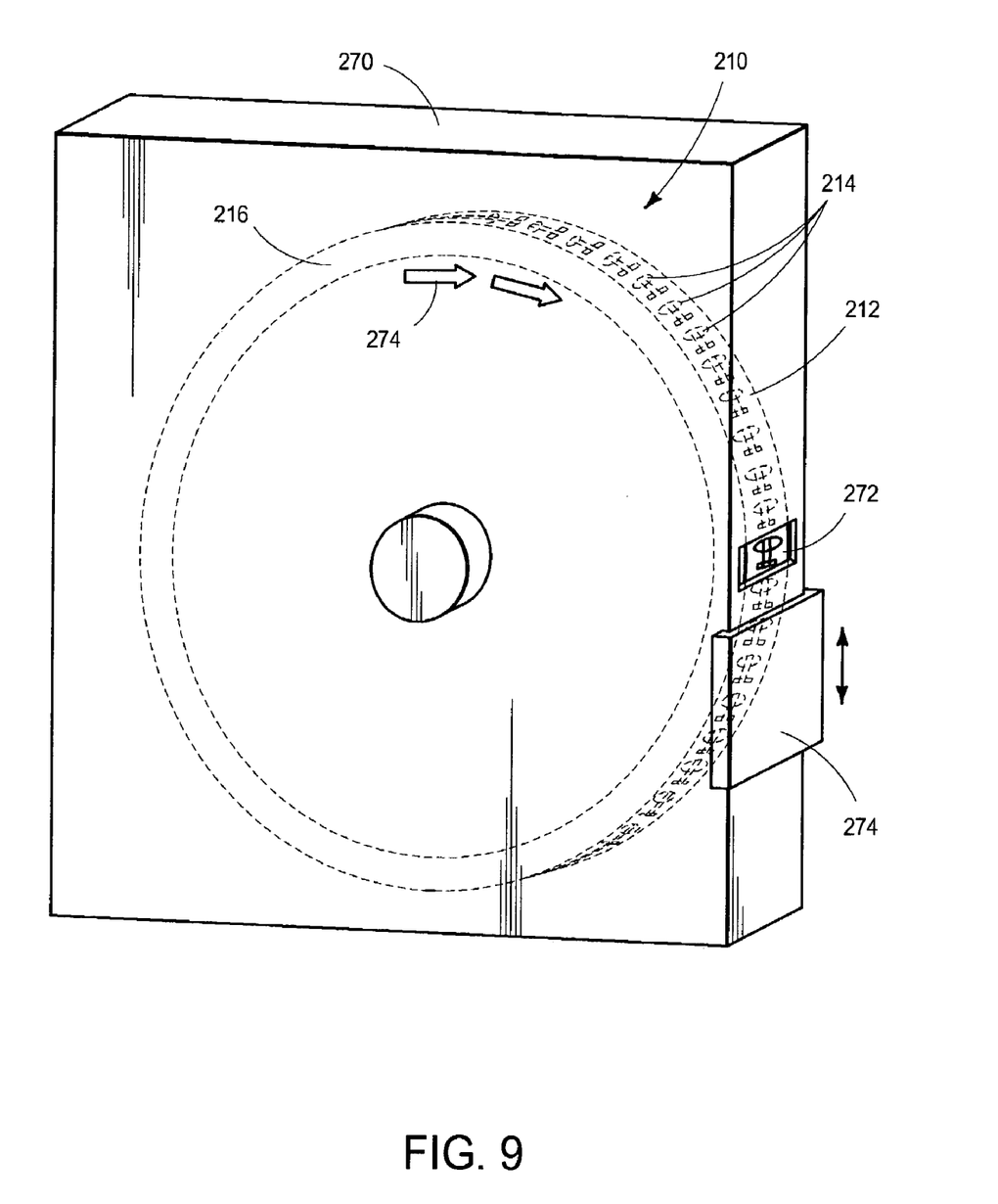
FIG. 9 is a perspective view of an alternative embodiment of a multiple use analyte sensing assembly according to the present invention.
Figure 10:
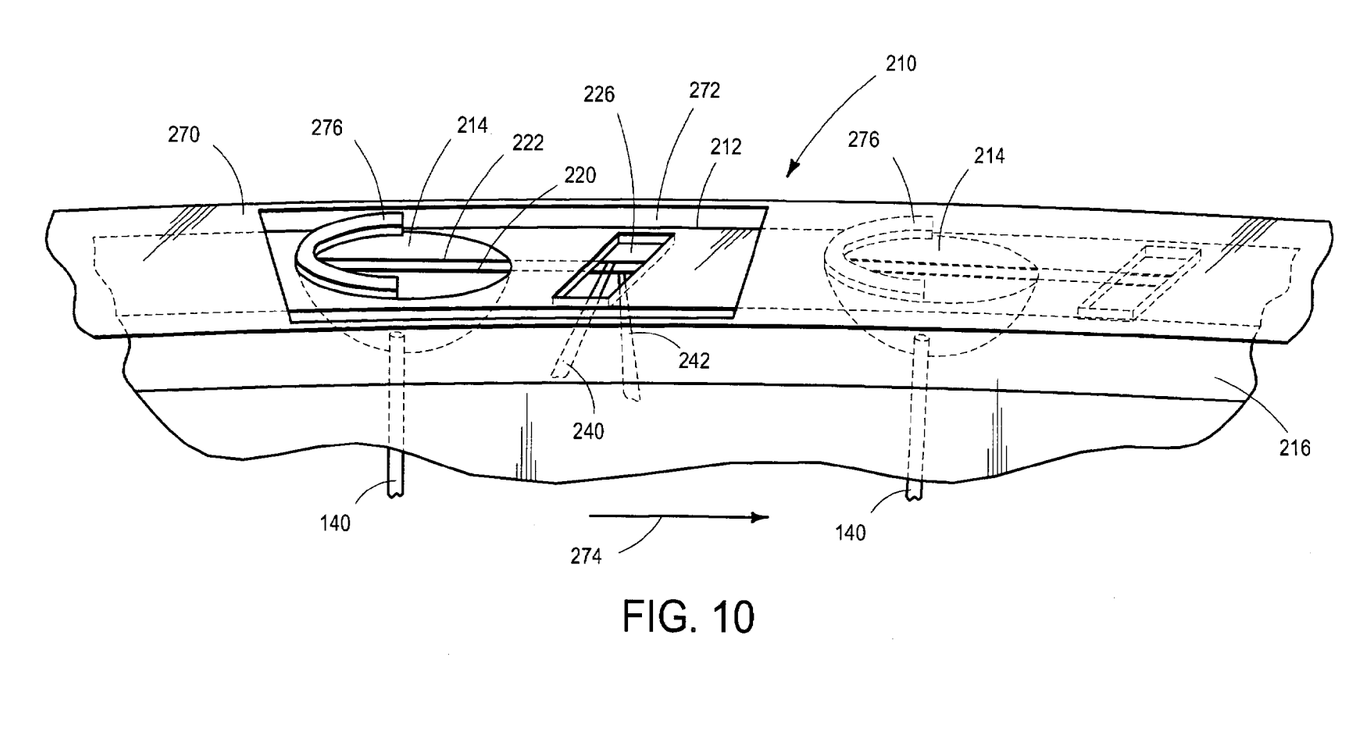
FIG. 10 is a perspective view of a portion of the analyte sensing assembly of FIG. 9.
Figure 11:
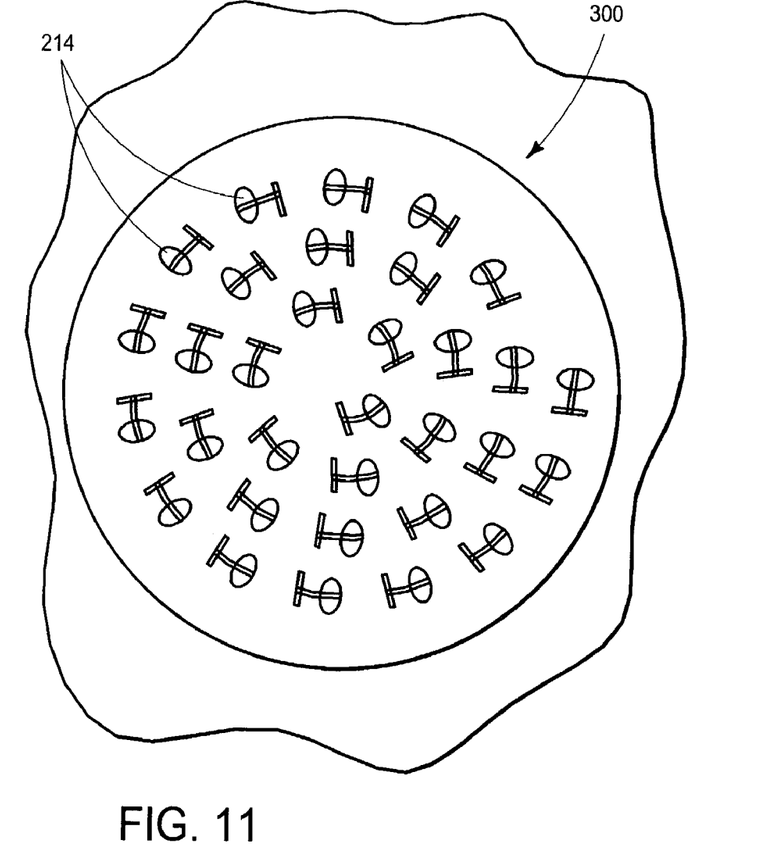
FIG. 11 is an expanded perspective view of a portion of the analyte sensing assembly of FIG. 9.

In the embodiment of FIGS. 9-12, the lancet assembly 140 may be the same as assembly 140 of FIG. 10 or assembly 140' of FIG. 11 and may fit into pocket 214 in similar manner.

Figure 12:
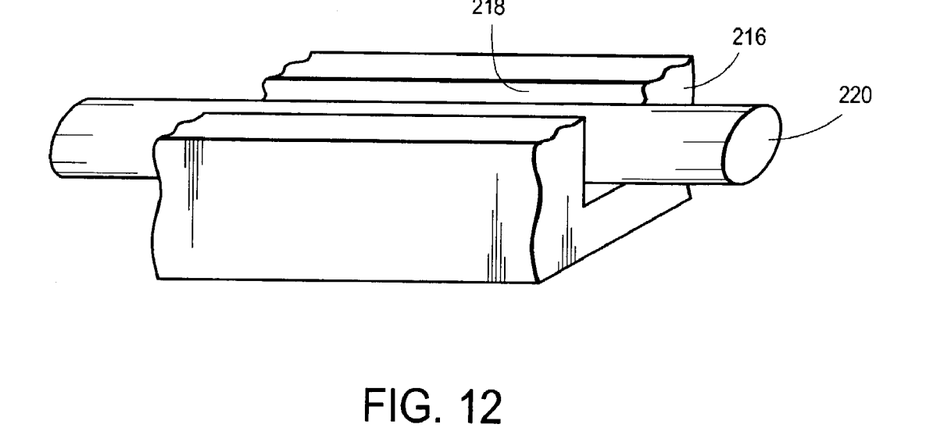
FIG. 12 is side view of an alternative embodiment of an analyte sensing assembly, according to the present invention.

FIG. 12 shows an embodiment which may be the same as that of FIGS. 9-11, but in which the active elements, ie. pockets and wires, are arrayed along the side of the drum 300 shown.

Figures 16, 17:
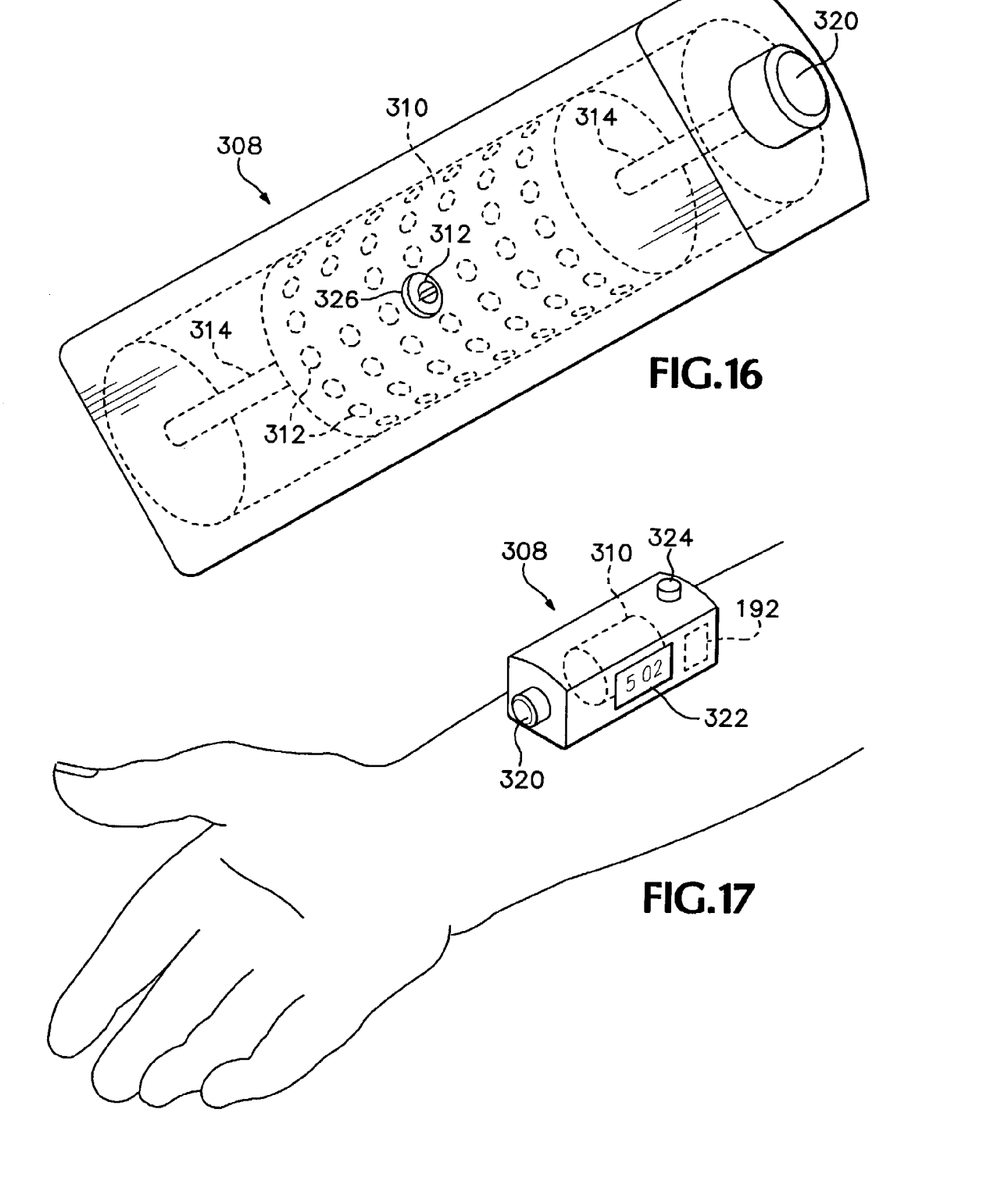
FIG. 16 is a perspective view of a preferred embodiment of a multiple use analyte sensor according to the present invention.
FIG. 17 is a perspective view of the analyte sensor of FIG. 16, in use.

FIGS. 16 and 17 show a compact module 308 according to the present invention, in perspective view and also in use. A drum 310 includes a multiplicity of blood traps 312, each of which is moved, in turn, to line up with aperture 326. As described with respect to the embodiment of FIG. 2, each row of traps 312 shares a separate wire assembly 112' (FIG. 2). Accordingly, between each pair of measurements drum 310 is rotated so that a wire assembly 112' that has not been used for at least one full rotation of the drum 310 will be used, to avoid contamination of the current measurement by blood drying from past measurements. After each full rotation of drum 310, drum 310 is moved axially along rod 314 to arrive at a new circumference of traps 312. Rod 314 is moved by a stepper motor 320, powered by a small battery (not shown) and controlled by logic subunit 192. Measurements are displayed on a small liquid crystal display 322 on the side of unit 308. A button 324 permits a user to start the measurement process. The embodiment shown in FIG. 16 has ninety-eight traps, enough for a number of days of measurement, is inexpensive to produce and easy to use.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow. In this application the term "animal" includes humans.

The invention claimed is:

1. A method of making a multiple use analyte sensing assembly, comprising:
providing an article having a surface that defines a set of pockets;
providing an analyte detection coated wire assembly; and
placing said wire assembly on said article so that said wire assembly traverses at least a plurality of pockets of said set of pockets, wherein said wire assembly traverses said plurality of pockets by being suspended over each of said plurality of pockets.

2. The method of claim 1 further comprising providing a sheet having a set of apertures coincident to said plurality of pockets and placing said sheet over said article so that said apertures are aligned to said plurality of pockets, thereby covering said wire assembly between said plurality of pockets.

3. The method of claim 1, wherein said article is in the form of a flat sheet.

4. The method of claim 1, wherein said article is in the form of a drum having a radially exterior surface, with said pockets arranged about said radially exterior surface.

5. The method of claim 1, wherein said plurality of pockets may be grouped into pairs of adjacent pockets and further including the step of cutting said wire assembly between each said pair of adjacent pockets.

6. The method of claim 1, further comprising:
providing a housing having a housing aperture;
placing said article having a surface that defines a set of pockets into said housing having a housing aperture; and
providing and installing into said housing an article movement assembly adapted to permit a user to move said article relative to said housing so that each of said plurality of pockets may be moved in sequence into a position corresponding to said housing aperture.

7. The method of claim 6, wherein said plurality of pockets may be grouped into pairs of adjacent pockets and further including the step of cutting said wire assembly between each said pair of adjacent pockets, thereby creating wire assembly segments corresponding to each of said plurality of pockets.

8. The method of claim 7, further including providing access to said wire assembly near each of said plurality of pockets and providing a coated wire contacting assembly adapted to conductively contact each said wire assembly segment when said corresponding pocket is moved into said position corresponding to said housing aperture.

9. A multiple use analyte sensing assembly, comprising:
an article having a surface that defines a set of pockets for collecting a sample containing analyte, and defining a pocket assembly for each pocket of said set of pockets, each said pocket assembly including:
an analyte sensing active electrode;
a reference electrode; and
a lancet;
wherein a plurality of said analyte sensing active electrodes are formed from a single continuous conductive element;
a housing having a housing aperture; and
an article movement assembly adapted to move said article relative to said housing so that each said pocket assembly may be moved into alignment to said housing aperture.

10. The assembly of claim 9 wherein said article also defines a slot between said pockets and wherein said single continuous conductive element resides in said slot and intersects each said pocket.

11. The assembly of claim 9 further including an apertured layer that covers said single continuous conductive element between said pockets.

12. The assembly of claim 9, wherein said article is in the form of a flat sheet.

13. The assembly of claim 9, wherein said article is in the form of a disk having a radially exterior surface, with said pockets arranged about said radially exterior surface.

14. The assembly of claim 13, wherein said pockets are arranged in a helical pattern about said radially exterior surface of said disk.

15. The assembly of claim 9, wherein said article is in the form of a disk having an axially exterior surface, with said pockets arranged about said axially exterior surface.

16. A method of making a multiple use analyte sensing assembly, comprising:

provinding an article having a surface that defines a set of pockets;

providing an analyte detection coated wire assembly; and placing said wire assembly on said article so that said wire assembly traverses at least a plurality of said pockets, wherein said article having a surface that defines a set of pockets also defines a slot between said pockets and wherein said wire assembly is threaded through said slot to intersect each said pocket.

17. A method of making a multiple use analyte sensing assembly, comprising:

providing an article having a surface that defines a set of pockets;

providing an analyte detection coated wire assembly; and placing said wire assembly on said article so that said wire assembly traverses at least a plurality of said pockets, wherein a liquid adhesive is applied to said coated wire assembly between each said pocket.

* * * * *